United States Patent [19]

Janata et al.

[11] 3,966,580

[45] June 29, 1976

[54] NOVEL PROTEIN-IMMOBILIZING HYDROPHOBIC POLYMERIC MEMBRANE, PROCESS FOR PRODUCING SAME AND APPARATUS EMPLOYING SAME

[75] Inventors: Jiri A. Janata; Jarmila Janata, both of Salt Lake City, Utah

[73] Assignee: The University of Utah, Salt Lake City, Utah

[22] Filed: Sept. 16, 1974

[21] Appl. No.: 506,464

[52] U.S. Cl. .............................. 204/195 B; 195/63; 195/68; 195/DIG. 11; 195/103.5 R; 195/127; 204/296; 427/307; 324/30 R
[51] Int. Cl.$^2$ ................ G01N 27/30; G01N 27/46; G01N 31/14; G01N 33/16
[58] Field of Search ........... 204/296, 195 M, 195 B, 204/1 T; 260/6, 8; 117/138.8 B; 195/63, 68, DIG. 11, 103.5 R–127; 427/322, 307, 399; 428/474

[56] References Cited
UNITED STATES PATENTS

| 3,574,062 | 4/1971 | Sato | 195/63 |
|---|---|---|---|
| 3,843,443 | 10/1974 | Fishman | 195/63 |
| 3,843,446 | 10/1974 | Vieth et al. | 195/68 |

OTHER PUBLICATIONS

E. K. Bauman et al., Analytical Chemistry, pp. 1378–1381, vol. 37, No. 11, Oct. 1965.

Klaus Mosbach, Scientific American, pp. 26–33, vol. 224, No. 3, Mar. 1971.

Primary Examiner—G. L. Kaplan
Attorney, Agent, or Firm—Trask & Britt

[57] ABSTRACT

A protein-immobilizing hydrophobic polymeric membrane comprising an organic, hydrophobic polymeric substrate with a specific protein reactive group pendant therefrom in preselected concentration is disclosed. The protein reactive groups is a free group of a hydrocarbon chain which has one end thereof absorbed into the surface of said polymeric substrate; said free group, generally at the end of said chain, covalently bonding with a protein molecule. The concentration of protein reactive sites is sufficiently low that the polymeric substrate retains its hydrophobic character. An electrode coated with a protein-immobilized membrane, i.e., a membrane having a hydrocarbon chain to which a protein molecule is attached, provides, in conjunction with a reference electrode, an electrically sensitive system for measuring change in concentration of a compound in solution where said compound selectively reacts with the immobilized protein.

10 Claims, 3 Drawing Figures

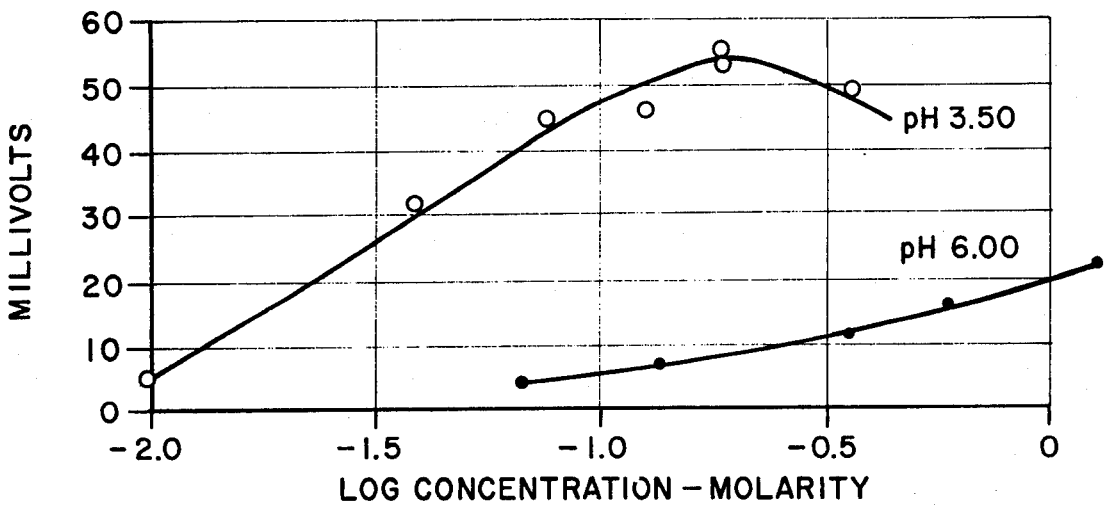
Fig. 1. DEPENDENCE OF POTENTIAL ON CONCENTRATION OF MANNAN AT 25°C
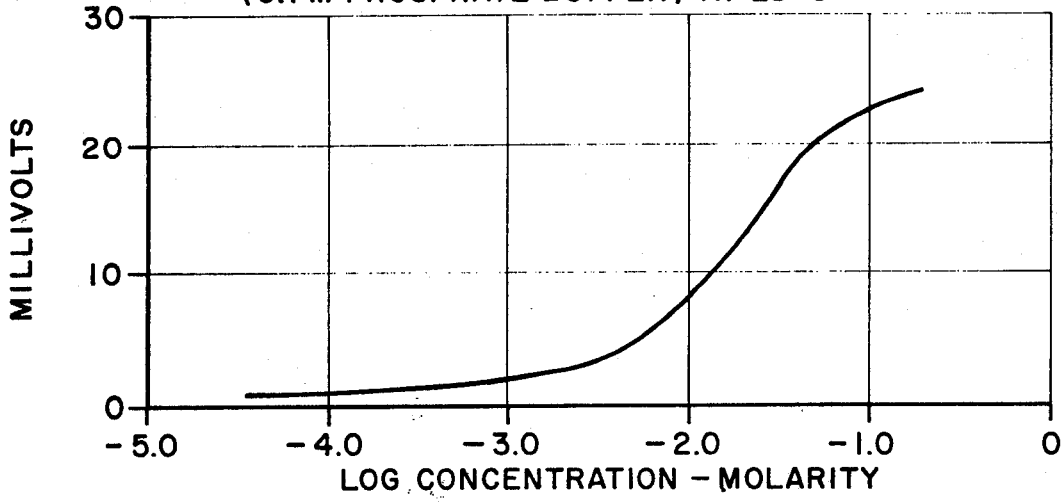
Fig. 2. CONCENTRATION DEPENDENCE FOR MANNOSE AT pH 6.00 (0.1 M PHOSPHATE BUFFER) AT 25°C
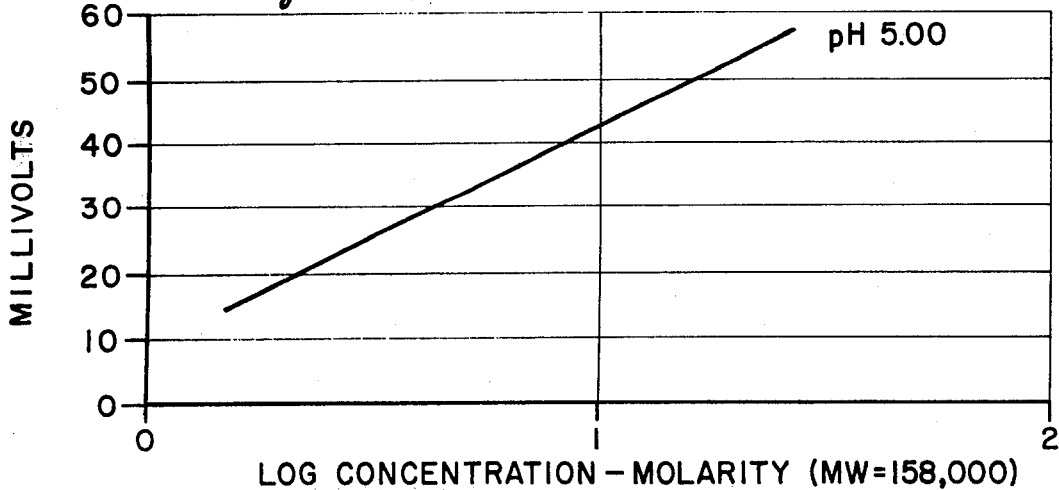
Fig. 3. CONCENTRATION DEPENDENCE FOR 7S γ GLOBULIN AT 25°C

3,966,580

NOVEL PROTEIN-IMMOBILIZING HYDROPHOBIC POLYMERIC MEMBRANE, PROCESS FOR PRODUCING SAME AND APPARATUS EMPLOYING SAME

BACKGROUND OF INVENTION

The specific reaction of a particular protein with another particular protein is well known, for example, the development within animals of a specific antibody to combat a particular antigen is well known. This specificity of one protein for another has been utilized in affinity chromatography to separate a specific protein which was present in a particular solution.

The selective reaction between two compounds exists for other compounds besides proteins, for example, enzymes and poly and monosaccharides selectively react with specific compounds, and is identified herein as an immunochemical reaction.

Affinity chromatographic materials, e.g., column packing objects, are prepared from hydrophilic polymeric surfaces which, by their polar nature, have reactive sites to which a protein reactive compound can be attached. The hydrophilic nature of the substrate is not affected by the attachment of the protein.

A protein molecule such as an antibody or antigen in a buffer solution has a net surface charge magnitude and polarity which depends on the isoelectric point of the protein and the composition of the buffer. This surface charge changes as a result of antibody-antigen reaction. Although the net change in electrical charge is of a magnitude to be detected, immobilization of a protein on a hydrophilic membrane is unsatisfactory because the ionic action of water on the polar groups of the hydrophilic substrate is so great that it masks the slight electrical potential change induced by the immunochemical reaction.

DESCRIPTION OF INVENTION

A hydrophobic membrane having the capability of immobilizing a protein has now been invented. The membrane comprises a thin substrate of a hydrophobic polymer capable of being swollen by solvent action and in which an aliphatic compound having a reactive terminal group can be absorbed from a solvent system. The hydrophobic membrane has pendant therefrom an essentially hydrocarbon chain which contains a protein reactive group, such as an oxirane group (epoxide) or other protein reactive group. The aliphatic chain may have linkages other than carbon-carbon bonds, such as ether bonds and, for the purposes of this invention, be considered an "essentially hydrocarbon chain".

The hydrophobic membrane having protein-immobilizing ability is used to encapsulate a highly conductive electrode, such as platinum. A protein, e.g., an antibody, having a selectivity for reaction with a particular protein (antigen) is reacted at the protein-reactive site. Immersion of such a coated electrode in association with a reference electrode into an aqueous solution provides an electrically sensitive system capable of measuring the change in electrical charge of the solution-polymer interface caused by the capture of a particular protein (antigen) by the electrode with an immunoreactive antibody. Also, the antigen may be immobilized on the membrane to selectively capture the antibody.

PROCESS DESCRIPTION

A hydrophobic polymeric membrane having selective immunochemical ability is prepared by forming a thin membrane of a hydrophobic polymer. The polymer is preferably one which is capable of being swollen with solvents, particularly aliphatic solvents. Polymers useful in the practice of this invention are those hydrophobic polymers which contain no pendant polar groups. Typical polymers for this purpose include thermoplastic polymers such as polyvinyl chloride, polystyrene, polyethylene, polypropylene, silicone rubber, polyurethane, polycarbonate, polytetrafluoroethylene and the like. Thermosetting polymers such as epoxy resins and cross-linked polyesters may also be used. Preferred polymers are those which may be coated upon an electrode by dip-casting or shrink-fitting.

The polymeric membrane is then treated with a solvent system capable of swelling the membrane for a period sufficient to result in swelling of the membrane. The solvent system contains, besides an appropriate solvent, an aliphatic compound having a reactive site thereon, preferably at or near one end of the hydrocarbon chain. The solvents used to swell the polymeric membrane are preferably those which may be readily removed by drying of the polymer. Thus, lower molecular weight solvents are generally preferred to higher molecular weight solvents. As indicated hereinafter, it is generally preferred that the solvent system contain solvents which are of a lower boiling point and more easily evaporated than the aliphatic compound having a reactive site thereon. A typical solvent mixture comprises petroleum ether of a 30° to 60°C boiling range and toluene. A typical aliphatic compound having a reactive site thereon is n-decanol. Other aliphatic compounds useful in the invention are n-hexanol, n-decylamine, n-hexylamine, n-decanoic acid and like compounds having a labile hydrogen.

After the polymeric membrane has been soaked in the solvent system for a period sufficiently long to permit swelling, the membrane is then dried in a vacuum oven at a temperature preselected to remove the solvent without removing substantial quantities of the aliphatic compound having a reactive site. When petroleum ether, toluene and solvents of similar boiling point range are utilized, a typical drying temperature is about 50° to 60°C, preferably under vacuum. Driving off the solvent results in a membrane having a low concentration of aliphatic groups pendant therefrom, said aliphatic groups having a reactive group thereon such as hydroxyl, amine or carboxyl.

As indicated, preferred solvents useful in practicing the invention are those which have a relatively low boiling range, for example, from about 30° to about 60°C. Typical solvents include cyclohexane, tetrahydrofuran (THF) and similar solvents which swell the membrane and carry in solution a small concentration of an aliphatic compound having a reactive site thereon. Choice of solvent depends upon the particular polymer used in the membrane. The polymers used herein have known solvents for swelling same.

After the polymeric membrane is dried, it is immersed in a solution containing a compound having a protein-reactive site and another reactive site reactive with the reactive group of the aliphatic compound now attached to the membrane. For example, if the reactive group of the aliphatic compound is a hydroxyl group, then a typical protein-reactive compound is epichlorohydrin wherein an epoxide ether is formed. Other reactive compounds which may be included in the solvent system in place of an aliphatic alcohol are such compounds as aliphatic amines, preferably primary and secondary amines, carboxyl containing aliphatic compounds and the like. These may be reactive with epichlorohydrin or with a bis-epoxide wherein a pair of oxirane rings are present for reaction. It is preferred generally to use reactive compounds wherein there is no likelihood of cross linking between a pair of pendant groups pending from the membrane surface. Thus, it is generally preferred that the protein-reactive compound have dissimilar reactive groups to preclude cross linking.

After the protein-reactive compound, i.e., compound containing an immobilizing group, e.g., epichlorohydrin, is reacted with the labile hydrogen of the aliphatic chain pending from the membrane surface, it is generally washed and placed in a solution containing the protein to be immobilized. A preferred reaction temperature is room temperature and it is generally preferred to allow one or two days for the reaction to proceed. The reaction is generally conducted in a slightly basic medium.

After the protein is attached, it is treated to wash off all residue of unreacted materials and further reacted with a compound to neutralize any unreacted protein-reactive, i.e., immobilizing, groups which remained after reaction with the protein molecule. Unreacted protein-reactive groups tend to be polar in nature and are also undesirable in that they react nonspecifically with proteins and could give erroneous results in a protein detection device.

In conducting the process according to the instant invention, it is generally preferred to use a reactive compound in the solvent system which has a sufficient chain length to permit the reactive group to be somewhat remote from the surface of the membrane. Generally, the reactive group of aliphatic compounds in the solvent system are those which are at least 6 carbon atoms in the main chain length. A preferred length is one in which the main chain of the aliphatic compound in the solvent system contains about 8 to 12 carbon atoms in the main chain. If the protein-reactive compound which is reacted therewith is of significant chain length so that the ultimate protein-reactive group is pendant from the surface by at least 6 carbon atoms, then the chain length of the reactive group in the solvent system need not be as long.

Following attachment of the aliphatic chain to the polymeric membrane, a series of treatments follow to provide a hydrophobic membrane having the ability to capture only a specific compound, as in an immunochemical reaction, such as exhibited by proteins, monosaccharides, polysaccharides and enzymes. The series of treatment for an aliphatic alcohol pendant from a polymeric membrane is illustrated as follows:

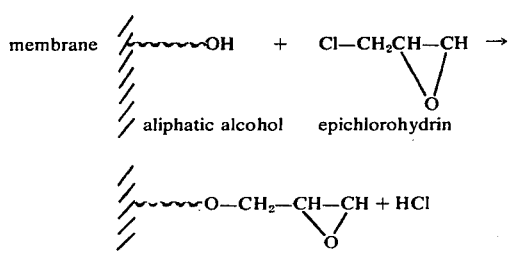

Proteins having amino groups react with the oxirane group to attach to the membrane to provide a membrane with an immobilized protein capable of capturing a specific protein in an immunochemical type reaction.

Other techniques for preparing an immobilized-protein membrane include:

a. Thiophosgene or isocyanate coupling

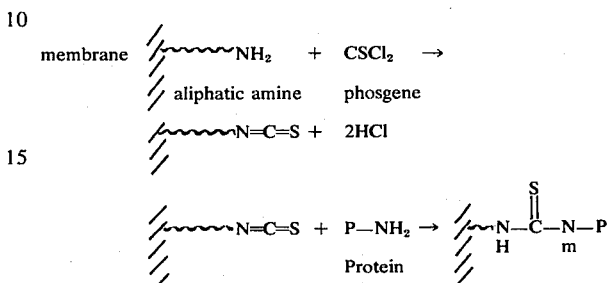

b. Azo coupling

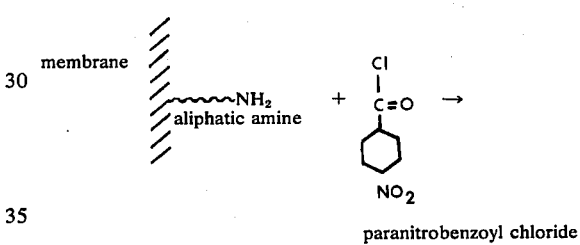

paranitrobenzoyl chloride

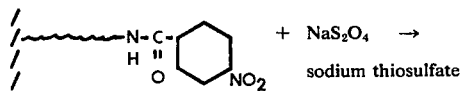

sodium thiosulfate

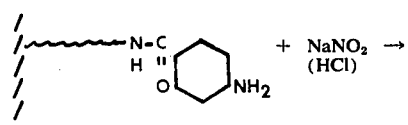

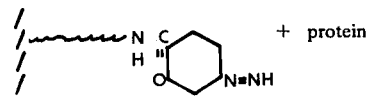

+ protein

Another protein reactive coupling system includes a diimide linkage between the aliphatic compound and protein molecule. An aliphatic compound with a carboxyl group is reacted with carbodiimide, the reaction product of which is reacted with a protein having an amino group.

The protein or other component of an immunochemically reactive pair, such as an enzyme, are very large molecules and it is likely that after immobilization of such a large molecule upon the reactive membrane, that other relatively large molecules, e.g., haptens, cannot penetrate through the barrier of large molecules to reach the membrane surface, although small molecules such as water may.

APPARATUS

The novel membranes of the instant invention are particularly useful inasmuch as they can be utilized in a device for electrically detecting the presence of a particular compound, both qualitatively and quantitatively in a given solution. The hydrophobic membrane has a low concentration of groups pendant from an aliphatic chain partially absorbed in the surface of the membrane which is utilized to coat an electrode. The pendant group is then reacted with one member of an antibody-antigen system or other immunochemical pair. Typical electrodes are glass encased platinum electrodes, although other electrodes may be encased in Teflon or other appropriate material. A sheath of the hydrophobic polymeric membrane containing a reactive group is formed on the measuring electrode in a thickness of about 10 to 50 microns, with a thickness of about 20 to 40 microns being preferred. A protein or other compound of an immunochemical pair is immobilized in the membrane. The measuring electrode is used in conjunction with a reference electrode. The two electrodes are immersed in a solution which contains a protein or other compound of the type sought to be identified. The measuring electrode and the reference electrode are electrically connected to a meter sensitive to very slight changes in electrical potential. As the particular protein is captured by the measuring electrode, the electrical potential at the polymer-solution interface changes. The slight change is detected by the meter, which has a high impedence in electrode circuitry, thus indicating the presence of the compound. By calibration, the meter may be used to determine quantitatively the amount of compound present in the solution.

EXAMPLE I

A protein-immobilized membrane is formed on a platinum electrode sealed in soft glass by dip casting the electrode in polyvinyl chloride solution. The coating was dried. A coating of about 25 microns in thickness was formed.

The polyvinyl chloride coated electrode was immersed in a solvent solution for three hours at room temperature. The solvent solution contained one part by volume of n-decanol, 4.5 parts by volume of petroleum ether and 4.5 parts by volume of toluene. The electrode was then placed in a vacuum oven at 50°C for a period of about 16 hours.

The dry electrode was then immersed in a solution containing 10% epichlorohydrin in 1 molar sodium hydroxide solution for 2 hours at about 60°C. The electrode was then washed with distilled water and placed in a solution containing a protein, for example, concanavalin A, at room temperature for a period of about 48 hours. The solution was a 0.5 molar sodium bicarbonate solution.

The measuring electrode was then removed from the solution, washed with 0.5 molar solution bicarbonate buffer, and with 0.1 molar potassium hydrogen phthalate buffer at a pH of 3.0 containing 1 molar sodium chloride, then with distilled water, then with 0.1 molar solution of tris (hydroxyl methyl) aminomethane buffer having a pH of 7.8 containing 0.5 molar solution ethanolamine. The ethanolamine is present to block any unreacted epoxy groups.

The measuring electrode was then electrically connected through a sensitive meter to a reference electrode. It is generally desired to have a large amount of impedence in the connecting system between the two electrodes. Concanavalin A is known to precipitate selectively certain branch polysaccharides containing non-reducing alpha-D-hexapyranosyl or beta-D-fructofuranosyl end groups. Yeast mannan belongs to this group and is known to be most reactive. The response of concanavalin A immunoelectrode to varying concentrations of yeast mannan at pH 6.0 and pH 3.5 is shown in FIG. 1. The potential of the system was shown to alter with the concentration of yeast mannan solution. No change of potential, however, was observed when a solution of agar was added to the measured solution. Agar is a polysaccharide which does not react with concanavalin A. The lack of change of electrical characteristics of the system when agar was added indicates that the conconavalin A selectivity was retained despite its immobilization on the hydrophobic membrane.

EXAMPLE II

Another example of the immunoelectrode specificity is illustrated in FIG. 3.

An immunoelectrode was prepared as in Example I. Rabbit anti-human 7S gamma-globulin was reacted with the pendant epoxide group. The immunoelectrode was then immersed in a solution of human 7S gamma-globulin at pH 5.00 wherein the concentration was changed. The change in concentration was detected electrically.

The immunochemical reaction between rabbit anti-human 7S gamma-globulin and human 7S gamma-globulin is known not to occur at pH 7.8. When the immunoelectrode containing immobilized rabbit anti-human 7S gamma-globulin was immersed in a solution of human 7S gamma-globulin, no electrical response was noted.

The immunochemical reactions remained even though one compound was immobilized on a hydrophobic polymeric membrane.

We claim:

1. A hydrophobic membrane having one member of an immunochemically reactive pair immobilized thereon comprising:
    a. a hydrophobic polymeric substrate swellable by an organic solvent,
    b. hydrocarbon chains of at least 6 carbon atoms in length partially absorbed into the surface of said polymeric substrate, said hydrocarbon chains having a reactive site reactive with one compound of an immunochemically reactive pair attached to its non-absorbed portion, and
    c. one member of an immunochemically reactive pair reacted with the reactive site of said hydrocarbon chain.

2. The membrane of claim 1 wherein the reactive sites of said hydrocarbon chains unreacted with one compound of an immunochemically reactive pair contain a reaction-blocking molecule.

3. The membrane of claim 1 wherein said reactive site of the hydrocarbon chain is an oxirane group.

4. The membrane of claim 1 wherein said organic polymeric substrate is swellable by aliphatic solvents.

5. The membrane of claim 1 wherein the said hydrocarbon chain is the reaction product of n-decanol and epichlorohydrin.

6. a hydrophobic membrane of claim 1 wherein the compound of an immunochemically reactive pair is a protein.

7. The hydrophobic membrane of claim 1 wherein the compound of an immunochemically reactive pair is an enzyme.

8. The hydrophobic membrane of claim 1 wherein the compound of an immunochemically reactive pair is a monosaccharide.

9. The hydrophobic membrane of claim 1 wherein the compound of an immunochemically reactive pair is a polysaccharide.

10. A quantitative device measuring electric potential difference for detecting presence of compounds reactive with an immobilized compound of an immunochemically reactive pair by utilization of an immunochemical reaction comprising:
   a. a reference electrode;
   b. a reactive electrode comprising:
      1. an electrical metal conductor;
      2. a sheath of hydrophobic polymeric membrane comprising:
         a. a hydrophobic polymeric substrate swellable by an organic solvent,
         b. hydrocarbon chains of at least 6 carbon atoms in length partially absorbed into the surface of said polymeric substrate, said hydrocarbon chains having a reactive site reactive with one compound of an immunochemically reactive pair attached to its non-absorbed portion,
         c. one member of an immunochemically reactive pair reacted with the reactive site of said hydrocarbon chain, and
   c. electrical conductor means connecting said reference electrode and measuring electrode through a meter sensitive to very slight changes in electrical potential.

* * * * *